United States Patent [19] [11] 4,214,103
Garman et al. [45] Jul. 22, 1980

[54] PURIFICATION OF BROMINATED ORGANIC PRODUCTS

[75] Inventors: John A. Garman; Rastko I. Mamuzic, both of West Lafayette, Ind.

[73] Assignee: Great Lakes Chemical Corporation, West Lafayette, Ind.

[21] Appl. No.: 965,091

[22] Filed: Nov. 30, 1978

[51] Int. Cl.² ............................................. C07C 41/12
[52] U.S. Cl. ........................... 568/639; 260/45.95 G; 252/8.1
[58] Field of Search ....................... 568/639; 252/8.1; 260/45.95 G

[56] References Cited

U.S. PATENT DOCUMENTS

| | | | |
|---|---|---|---|
| 2,022,634 | 11/1935 | Britton et al. | 568/639 |
| 2,076,430 | 4/1937 | Hanson et al. | 568/639 X |
| 3,192,272 | 6/1965 | Asadorian | 260/650 |
| 3,285,965 | 11/1966 | Jenkner | 568/639 |
| 3,366,694 | 1/1968 | Thompson | 568/639 |

FOREIGN PATENT DOCUMENTS 1029874 5/1966 United Kingdom .
1436657 5/1976 United Kingdom .

*Primary Examiner*—Bernard Helfin
*Attorney, Agent, or Firm*—Kirkland & Ellis

[57] ABSTRACT

Crude halogenated organic products, especially products consisting of partially halogenated diphenyl ethers alone or in admixture with other materials may be purified by contacting the crude brominated product with a finely divided basic solid such as a carbonate or bicarbonate of an alkali metal or ammonia for a time and at a temperature sufficient to enhance the purity thereof. The purification step may be performed in the presence of an organic solvent or by adding the basic solid directly to molten crude products in the presence of a small amount of water.

14 Claims, No Drawings

PURIFICATION OF BROMINATED ORGANIC PRODUCTS

BACKGROUND OF THE INVENTION

1. Field of the Invention

This invention relates to the purification of crude halogenated products containing residual free bromine, by-product hydrogen bromide, catalyst, and other impurities.

2. Description of the Prior Art

Numerous processes may be employed to replace nuclear hydrogen atoms partially with bromine in aromatic compounds such as diphenyl ether. Such bromination processes in general have involved use of an up to about 20% excess of bromine in various reaction media depending upon the particular aromatic compound to be brominated. Normally such bromination is undertaken in the presence of a bromination catalyst such as iron, aluminum, and their halides, especially if a higher degree of bromination is desired.

Alternatively, partially brominated aromatic compounds may be obtained by reacting the compound in the presence of a slight excess of bromine in the absence of any reaction solvent but likewise employing a small but catalytic amount of a bromination catalyst.

Regardless of the preparation processes employed, there are produced brominated products containing undesirable amounts of occluded free bromine, by-product hydrogen bromide, catalyst residue, and other materials which adversely affect the color of the product and which may diminish its thermal stability.

High levels of purity are frequently required for brominated aromatic compounds such as partially brominated diphenyl ethers which have found utility as flame retardant agents. In particular, it is important that such brominated products have extremely low levels of residual impurities such as free bromine, bromine-containing impurities, catalyst, and the like since the presence of such impurities can have undesirable effects on the compositions in which such compounds are used as flame retardant agents or for other purposes. Purity is particularly important from the standpoint of color and thermal stability under the processing conditions to which such compounds are subjected.

Purification of halogenated products such as the brominated diphenyl ethers obtained in the foregoing manner has heretofore been attempted by a variety of work-up procedures. Thus, British Pat. No. 1,436,657 suggests that a crude product mixture of tetra- and penta-bromodiphenyl ether be worked up by treating a solution of the crude product in methylene chloride with successive washes of sodium metabisulfite, sodium carbonate, and water.

British Pat. No. 1,029,874, relating to the production of tri-brominated biphenyls (colorless liquids at room temperature), employs dilute hydrochloric acid in the product work-up. U.S. Pat. No. 2,022,634, describing the preparation of mixtures of chlorinated or brominated diphenyl ethers having more than four but less than ten halogen atoms, purifies the product by air blowing following bromine introduction and, in the case of Examples 8–10, also employs chlorobenzene solvent in combination with alternate washes with dilute hydrochloric acid and sodium hydroxide.

U.S. Pat. No. 3,192,272 purifies tribrominated dialkylbenzenes by washing first with water and thereafter with aqueous sodium carbonate followed by fractional distillation.

None of the foregoing schemes have been totally satisfactory in obtaining brominated products having required levels of purity and, accordingly, it is a primary object of this invention to obtain a process for purification of halogenated products of the character described that is superior to the techniques that have heretofore been employed.

Another object is to provide a process of the character described for producing purified partially brominated diphenyl ethers of good color and thermal stability.

A still further object is to provide a purification method of the character described that may be economically employed in obtaining purified partially brominated diphenyl ethers.

SUMMARY OF THE INVENTION

The foregoing and other objects, advantages, and features of the present invention may be achieved with a process for purifying crude halogenated products such as partially halogenated diphenyl ethers, especially partially brominated diphenyl ethers, mixtures thereof, and blends thereof with other materials comprising the steps of contacting the crude product with an effective amount of a finely divided basic solid for a time and at a temperature sufficient to enhance the purity of the products and thereafter separating and recovering the purified product.

More particularly, it has been found that halogenated products such as partially chlorinated and partially brominated diphenyl ethers, mixtures thereof, and blends thereof with other materials may advantageously be purified in accordance with the method of this invention. The finely divided basic solid to be employed may be a carbonate or bicarbonate of an alkali metal or ammonia.

The process may be carried out with the crude product dissolved in an organic solvent preferably in the absence of water or, alternatively, the finely divided basic solid may be introduced into the crude product maintained at a temperature sufficient to keep it in a molten state in the presence of a small amount of water.

DESCRIPTION OF THE PREFERRED EMBODIMENTS

The process of this invention may be employed in the purification of crude halogenated products especially ring-chlorinated or ring-brominated aromatic compounds such as partially brominated and partially chlorinated diphenyl ethers. These materials may be produced by processes generally involving the addition of a slight stoichiometric excess of bromine and a bromination catalyst such as iron, aluminum, and their corresponding halides to the aromatic compound to be brominated. Such reactions may be carried out in the presence of an organic solvent, or the reaction may be carried out in the presence of bromine without other solvent being present.

The particular process by which such products are produced does not form a part of this invention, but in all events the crude products so produced contain occluded bromine, hydrogen bromide and catalyst residue.

The process of this invention provides a simple, expedient, and economical method for working up such a crude product mixture.

The basic purification step involves treatment of the crude product with a finely divided basic solid. Preferably, the basic solid is a carbonate or bicarbonate of an alkali metal or ammonia, although other basic solids may be employed. As noted, the solid should be added in finely divided form.

The purification step may be performed with the crude product dissolved in a suitable organic solvent such as toluene although other organic solvents, such as, for example, carbon tetrachloride, ethylene dibromide, benzene, methylene chloride, tetrachloroethane and the like may also be employed. Where the basic solid is added to the crude product in an organic solvent, it is preferred that water be excluded, and the solution is preferably maintained at an elevated temperature less than the reflux temperature of the solution. Thus, where the basic solid is added to the crude product in the solution, water is preferably excluded, and the basic solid added is preferably provided in anhydrous form.

Alternatively, the finely divided solid may be added directly to the crude product in the absence of the solvent at a temperature at which the crude product is molten. Where the basic solid is added to the molten crude product, a small but effective amount of water should be present and may conveniently be provided by supplying the basic solid in hydrated form (e.g., through the use of crystalline sodium carbonate decahydrate ($Na_2CO_3.10H_2O$) instead of the anhydrous salt, $Na_2CO_3$).

The optimum purification procedure involves agitating the solution of crude product in organic solvent with powdered basic solid for a time and at a temperature sufficient to effect enhanced purity.

Where crude octabromodiphenyl ether is the product to be purified, the procedure optimally involves obtaining a solution of crude octabromodiphenyl ether in toluene (0.4:1 W/W toluene/octabromodiphenyl ether) which is heated to a temperature of about 90° C., a temperature less than the 115° C. reflux temperature for octabromodiphenyl ether-toluene solutions. While agitating the solution, powdered anhydrous sodium carbonate (1% $Na_2CO_3$ W/W on octabromodiphenyl ether) is added. Agitation is continued for about one hour. Thereafter, the solution is filtered and the toluene solvent is then removed (e.g., by stripping under reduced pressure) in order to obtain purified octabromodiphenyl ether.

The amount of basic solid to be added is not critical. Preferably, about 1 or 2 percent solid by weight of the crude product may be employed. The post-addition agitation time is likewise not critical, but treatment times lying in the range of one-half hour to one hour are desirable. Longer agitation times may be employed but do not appear to be beneficial in terms of increased purity.

As noted, the basic solid may be alternatively added in the absence of a solvent to the crude product maintained in a molten state at elevated temperature. In the case of octabromodiphenyl ether maintained at a temperature of about 130° C., the process involves agitating molten crude octabromodiphenyl ether with hydrated sodium carbonate for one-half hour in a "closed" system (i.e., a system from which water may not escape) followed by continued agitation at the same temperature for an additional period of time in an open system from which the water is permitted to escape, followed by subsequent filtering. The same loading of basic solid is employed in this process as in the solvent process. Thus, 2.7 percent $Na_2CO_3.10H_2O$ (W/W on octabromodiphenyl ether), corresponding to 1% anhydrous $Na_2CO_3$ employed in the solvent process, is employed. The temperature of 130° C. selected for octabromodiphenyl ether is approximately the lowest temperature at which the product is sufficiently molten for effective agitation. While higher temperatures may be utilized, unnecessary thermal decomposition may be encountered, and it is thus desirable to employ the lowest temperature at which the product can be maintained in a molten state.

The presence of some water during the neat purification step is essential, the amount, however, not being critical. Desirably, an appropriate amount is applied by using crystalline sodium carbonate decahydrate as the basic solid. Alternatively, anhydrous sodium carbonate may be employed, but an additional source of a small but effective amount of water must be supplied. As in the case of the solvent process, the agitation times does not appear to be critical, with longer agitation times resulting in only slight improvement. It appears that the optimum treatment involves closed agitation for one-half hour followed by a second one-half hour under open system conditions in order to permit the water to escape.

The process of this invention may be illustrated in the following examples.

EXAMPLE I

Purification of Octabromodiphenyl Ether

A toluene solution of crude octabromodiphenyl ether (0.4:1 w/w toluene:crude) was stirred mechanically with sodium carbonate, $Na_2CO_3$(1% W/W on octabromodiphenyl ether) at 90° C. for one hour. The suspension obtained was then filtered under reduced pressure while still warm through a sintered glass funnel, and the toluene solvent was then stripped under vacuum.

The color value (expressed as percent transmission of a 10% w/w toluene solution in a 1-inch cell at 400 millimicrons), the level of iron catalyst (expressed in parts per million of iron), and the percent bromine are reported in Table I. Table I also reports product yields, comparing the yield of the purified products and of the crude products, both based on the diphenyl ether (DPO) starting material.

EXAMPLE II

Purification of Octabromodiphenyl Ether

Molten crude octabromodiphenyl ether was stirred mechanically in a flask equipped with a reflux condenser with sodium carbonate decahydrate, $Na_2CO_3.10H_2O$ (2.7% W/W on octabromodiphenyl ether) at 130° C. for one-half hour. Water was thereafter removed from the system by removing the reflux condenser and passing a stream of air above the surface of the melt while maintaining it at 130° C. for an additional one-half hour. The purified product was obtained by filtering the molten mixture under reduced pressure at 130° C. through a jacketed heated sintered glass funnel. Product properties and yield data for Example II are also reported in Table I.

TABLE I

Purification of Octabromodiphenyl Ether

| | Example I | Example II |
|---|---|---|
| Product Properties | | |
| Color (% T) | 81 | 78 |
| Iron | 1 | 2 |
| % Br | 78.1 | 79.1 |
| Yield (on DPO) (%) | | |
| Crude | 95.8 | 95.8 |
| Purified | 95.2 | 88.6 |

EXAMPLE III

Purification of Pentabromodiphenyl Ether

Crude pentabromodiphenyl ether was dissolved in toluene (0.4:1 w/w toluene:crude) and treated with anhydrous sodium carbonate (1% W/W on pentabromodiphenyl ether) for one hour at a temperature of 90° C. with agitation. Thereafter, the solution was filtered, and the toluene solvent was removed by stripping to yield the purified pentabromodiphenyl ether product. Product properties are reported in Table II for purified material of this Example as well as for the crude pentabromodiphenyl ether starting material.

EXAMPLE IV

Using the same procedure set forth in Example II, crude pentabromodiphenyl ether was heated to a temperature of 130° C. and maintained at that temperature in a molten state with hydrated sodium carbonate (2.7% W/W on pentabromodiphenyl ether). Agitation was continued in a closed system for one-half hour, and thereafter the reflux condenser was removed, and air was passed over the surface of the molten material to permit the water to escape while continuing agitation for one-half hour. The purified product was obtained by passing the molten material through a jacketed, heated sintered funnel maintained at 130° C. The properties of the purified product are set forth in Table II.

TABLE II

Purification of Pentabromodiphenyl Ether

| Product Properties | Pentabromo-diphenyl Ether | Example III | Example IV |
|---|---|---|---|
| Color (% T) | 32 | 43 | 45 |
| Acidity (mg. KOH/g.) | 0.06 | 0.06 | 0.08 |
| Iron Content (ppm) | 4 | 1 | 1 |

EXAMPLE V

Purification of Pentabromodiphenyl Ether Blends

The technique of this invention may also be employed to purify blends of partially brominated diphenyl ethers with other material. In this example, a blend composed of 85% pentabromodiphenyl ether and 15% 2-ethylhexyl diphenyl phosphate was purified in the following manner. A solution of the blends in toluene (0.4:1 w/w toluene:blend) was maintained at a temperature of 90° C., and anhydrous sodium carbonate (1% W/W on the blend) was added and the mixture subjected to agitation for one hour. The solution was filtered, and the solvent stripped to obtain the purified product, the properties of which are given in Table III.

EXAMPLE VI

Purification of Pentabromodiphenyl Ether Blends

Using the procedure of Examples II and IV, the pentabromodiphenyl ether-2-ethylhexyl diphenyl phosphate blend was heated to 130° C., and sodium carbonate decahydrate (2.7% W/W on the blend) was added and subjected to agitation in the closed system for one-half hour. Thereafter, the system was opened in order to permit water to escape. The molten mixture was filtered to obtain the purified blend. Relevant properties of the blend are given in Table III.

TABLE III

Purification of Pentabromodiphenyl Ether Blends

| Product Properties | Unpurified Blend | Example V | Example VI |
|---|---|---|---|
| Color (% T) | 43 | 50 | 46 |
| Iron (ppm) | 11 | 2 | 1 |
| Acidity (mg. KOH/g.) | 0.08 | 0.05 | 0.04 |

EXAMPLE VII

Purification of Hexabromodiphenyl Ether

Crude hexabromodiphenyl ether was dissolved in toluene (0.4:1 w/w toluene:crude) and treated with anhydrous sodium carbonate (1% W/W on hexabromodiphenyl ether) for one hour at a temperature of 90° C. with agitation. Thereafter, the solution was filtered, and the toluene solvent was removed by stripping to yield the purified hexabromodiphenyl ether product. Product properties are reported in Table IV for purified material of this Example.

TABLE IV

Purification of Hexabromodiphenyl Ether

| Product Properties | Example VII |
|---|---|
| Color (% T) | 73 |
| Acidity (mg. KOH/g) | 0.17 |
| Iron Content (ppm) | <1 |

EXAMPLE VIII

Purification of Heptabromodiphenyl Ether

Crude heptabromodiphenyl ether was dissolved in toluene (0.4:1 w/w toluene:crude) and treated with anhydrous sodium carbonate (1% W/W on heptabromodiphenyl ether) for one hour at a temperature of 90° C. with agitation. Thereafter, the solution was filtered, and the toluene solvent was removed by stripping to yield the purified heptabromodiphenyl ether product. Product properties are reported in Table V for purified material of this Example.

TABLE V

Purification of Heptabromodiphenyl Ether

| Product Properties | Example VIII |
|---|---|
| Color (% T) | 62 |
| Acidity (mg. KOH/g.) | 0.16 |
| Iron Content (ppm) | 3 |

By use of the purification procedure of this invention, a simple, economical and highly effective method of purifying crude halogenated products such as crude partially brominated diphenyl ethers and mixtures and blends thereof is achieved. In particular, by use of a simple one step treatment of crude product in solution or in molten form with a finely divided basic solid, the complex multistep work-ups of the prior art need not be employed yet highly purified materials are readily obtained.

We claim:

1. A process, for purifying a member selected from the group consisting of partially brominated diphenyl ethers, mixtures thereof, and blends thereof with other materials comprising the steps of:
   dissolving the member in an organic solvent and maintaining the resulting solution at an elevated temperature below the reflux temperature of the solution while substantially excluding water from the solution;
   adding a finely divided basic solid to the solution and agitating for a time sufficient to enhance the purity of the product;
   thereafter filtering the solution; and
   thereafter stripping the solvent therefrom.

2. A process, as claimed in claim 1, wherein the member is octabromodiphenyl ether.

3. A process, as claimed in claim 1, wherein the member is pentabromodiphenyl ether.

4. A process, as claimed in claim 1, where the member is hexabromodiphenyl ether.

5. A process, as claimed in claim 1, wherein the member is heptabromodiphenyl ether.

6. A process, as claimed in claim 1, wherein the member is a blend comprising a partially brominated diphenyl ether.

7. A process, as claimed in claim 1, wherein the finely divided basic solid is anhydrous sodium carbonate.

8. A process for purifying a member selected from the group consisting of partially brominated diphenyl ethers, mixtures thereof, and blends thereof with other materials comprising the steps of:
   applying sufficient heat to the member in order to maintain it in a molten state;
   adding a finely divided basic solid to the mixture in the presence of a small but effective amount of water with agitation and continuing the agitation for a first period of time in a closed system which retains water and for a second period of time in an open system from which water escapes; and
   thereafter filtering the molten member to recover the purified member.

9. A process, as claimed in claim 8, wherein the finely divided basic solid is crystalline sodium carbonate decahydrate.

10. A process, as claimed in claim 8, wherein the member is octabromodiphenyl ether.

11. A process, as claimed in claim 8, wherein the member is pentabromodiphenyl ether.

12. A process, as claimed in claim 8, wherein the member is hexabromodiphenyl ether.

13. A process, as claimed in claim 8, wherein the member is heptabromodiphenyl ether.

14. A process, as claimed in claim 8, wherein the member is a blend comprising a partially brominated diphenyl ether.

* * * * *